United States Patent [19]

Zaiger et al.

[11] Patent Number: Plant 7,194

[45] Date of Patent: Mar. 13, 1990

[54] PEACH TREE "RED JACK"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 315,537

[22] Filed: Feb. 27, 1989

[51] Int. Cl.[4] ..... A01H 5/00

[52] U.S. Cl. ..... Plt./43

[58] Field of Search ..... Plt./43

*Primary Examiner*—James R. Feyrer

[57] ABSTRACT

A new and distinct variety of peach tree which the following unique combination of desirable features:

1. A low winter chilling requirement of approximately 150 hours.
2. Producing very firm fruit with good storage and shelf life.
3. Fruit with attractive red skin color.
4. The regular and heavy production of fruit.
5. Early maturity of the fruit.
6. Fruit with good flavor and eating quality.
7. Vigorous and upright growth.

1 Drawing Sheet

ORIGIN OF THE VARIETY

The new variety of peach tree was originated by us in the experimental orchard located near Modesto, Calif. as a first generation cross between two seedling selections with the field identification numbers 37G850 and 24GA678. The female parent 37G850 originated from a second generation seedling of Ruby Gold Nectarine (U.S. Plant Pat. No. 3101) crossed with a low chilling peach of unknown origin. The pollen parent 24GA678 originated from a second generation seedling of a cross between Sun Red Nectarine (non-patented) and Royal April Peach (U.S. Plant Pat. No. 3,411).

ASEXUAL REPRODUCTION OF THE VARIETY

The present variety of peach tree was asexually propagated by budding, as performed in the experimental orchard located near Modesto, Calif., and shows that such reproductions of said characteristics run true to form and are established and transmitted through succeeding propagations.

SUMMARY OF THE VARIETY

The new and distinct variety of peach tree is of large size, vigorous, upright growth and a regular and productive bearer of medium size, yellow flesh, clingstone fruit with an attractive red skin color, good flavor and eating quality. The fruit is further characterized by developing red skin color 8 to 10 days before ripening, having very firm flesh which allows the fruit to become fully mature before harvest while maintaining good shipping and storage quality. The fruit maturing in the early season, May 20, 1987 in Modesto, Calif., has a higher degree of red skin color and more fruit firmness than most all other early maturing commercial varieties with a chilling requirement of approximately 150 hours.

BRIEF DESCRIPTION OF THE PHOTOGRAPHS

The accompanying photographic illustrations show typical specimens of the fruit and foliage of our new variety, with the upper and lower surface of the leaves, an exterior and sectional view of the fruit with the stone being shown. The illustrations were taken shortly after being picked at maturity, (firm ripe) and the colors are as nearly true as reasonably possible in a color representation of this type.

DESCRIPTION OF THE VARIETY

The detailed botanical description of the foliage and fruit of the new variety of peach tree is based upon observations of the specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Density.*—Medium dense.
- *Form.*—Upright.
- *Production.*—Productive.
- *Bearer.*—Regular.

Trunk:
- *Size.*—Medium to stocky.
- *Texture.*—Medium to shaggy.

Branches:
- *Size.*—Medium.
- *Surface.*—Smooth to medium rough.
- *Lenticels.*—Medium number. Medium size.
- *Color.*—Brown to grayish brown.

Leaves:
- *Size.*—Large. Average length — 7¼". Average width — 1⅝".
- *Form.*—Lanceolate. Pointed.
- *Thickness.*—Medium.
- *Texture.*—Medium.
- *Margin.*—Crenate.
- *Petiole.*—Medium length. Medium thickness.
- *Gland.*—Number varies from 1 to 3. Average number 2. Located on base of leaf and upper portion of petiole. Predominately globose — some leaves have reniform.
- *Color.*—Upper surface — green (28-F-6) to (28-F-7). Lower surface — dull green (29-E-7). to (29-E-8).

Flower buds:
- *Size.*—Medium.
- *Length.*—Medium.

Flowers:

*Blooming period.*—Feb. 8, 1987 to Feb. 15, 1987.
*Size.*—Medium. Non-showy.
*Pollen.*—Present.
*Color.*—Pink.

Fruit:
*Maturity when described.*—Firm ripe.
*Date of first picking.*—May 17, 1987.
*Date of last picking.*—May 23, 1987.
*Size.*—Medium. Average diameter axially — $2\frac{3}{8}''$. Average transversely in suture plane — $2\frac{3}{8}''$.
*Form.*—Globose — nearly symmetrical.
*Suture.*—Very shallow.
*Ventral surface.*—Rounded.
*Cavity.*—Rounded to elongated in suture plane. Average depth — $\frac{1}{2}''$. Average breadth — $\frac{3}{4}''$.
*Apex.*—Varies from rounded to slight depression.

Skin:
*Thickness.*—Medium.
*Texture.*—Tough, tenacious to flesh.
*Tendency to crack.*—None.
*Down.*—Moderate to heavy.
*Color.*—Yellow ground color (5-A-7) to (5-A-8). Nearly overspread with red (8-A-8) to (8-B-8).

Flesh:
*Juice.*—Moderate.
*Texture.*—Very firm, meaty.
*Ripens.*—Relatively even.
*Flavor.*—Good.
*Aroma.*—Moderate.
*Eating quality.*—Good.
*Color.*—Yellow (4-A-6) to (4-A-8). Pit cavity — grayish yellow (4-B-6) to (4-B-7).

Stone:

*Type.*—Clingstone.
*Size.*—Large. Average length — $1\frac{1}{8}''$. Average width — $1''$. Average thickness — $\frac{5}{8}''$.
*Form.*—Ovid.
*Base.*—Straight to slightly oblique.
*Apex.*—Usually rounded — some pointed.
*Sides.*—Nearly equal.
*Surface.*—Irregularly furrowed.
*Color.*—Brown to reddish brown (8-C-6) to (8-D-6).
*Tendency to crack.*—Slight.

Use: Dessert.
Shipping quality: Good.
Keeping quality: Good.

The tree and its fruit herein described may vary in slight detail due to climatic, soil and cultural practices under which the tree may be grown; the present description being that of the new variety grown under the ecological conditions prevailing at Modesto, Calif.

The following is claimed:

1. A new and distinct variety of peach tree substantially as illustrated and described, with a low winter chilling requirement of approximately 150 hours and is of large size, vigorous, upright in growth and a regular and productive bearer of early maturing, medium size, yellow flesh, clingstone fruit with good flavor and eating quality; the fruit is further characterized by coloring 8 to 10 days before maturity and having firmer flesh and more attractive red skin color than most all other early maturing commercial varieties with a low winter chilling requirement.

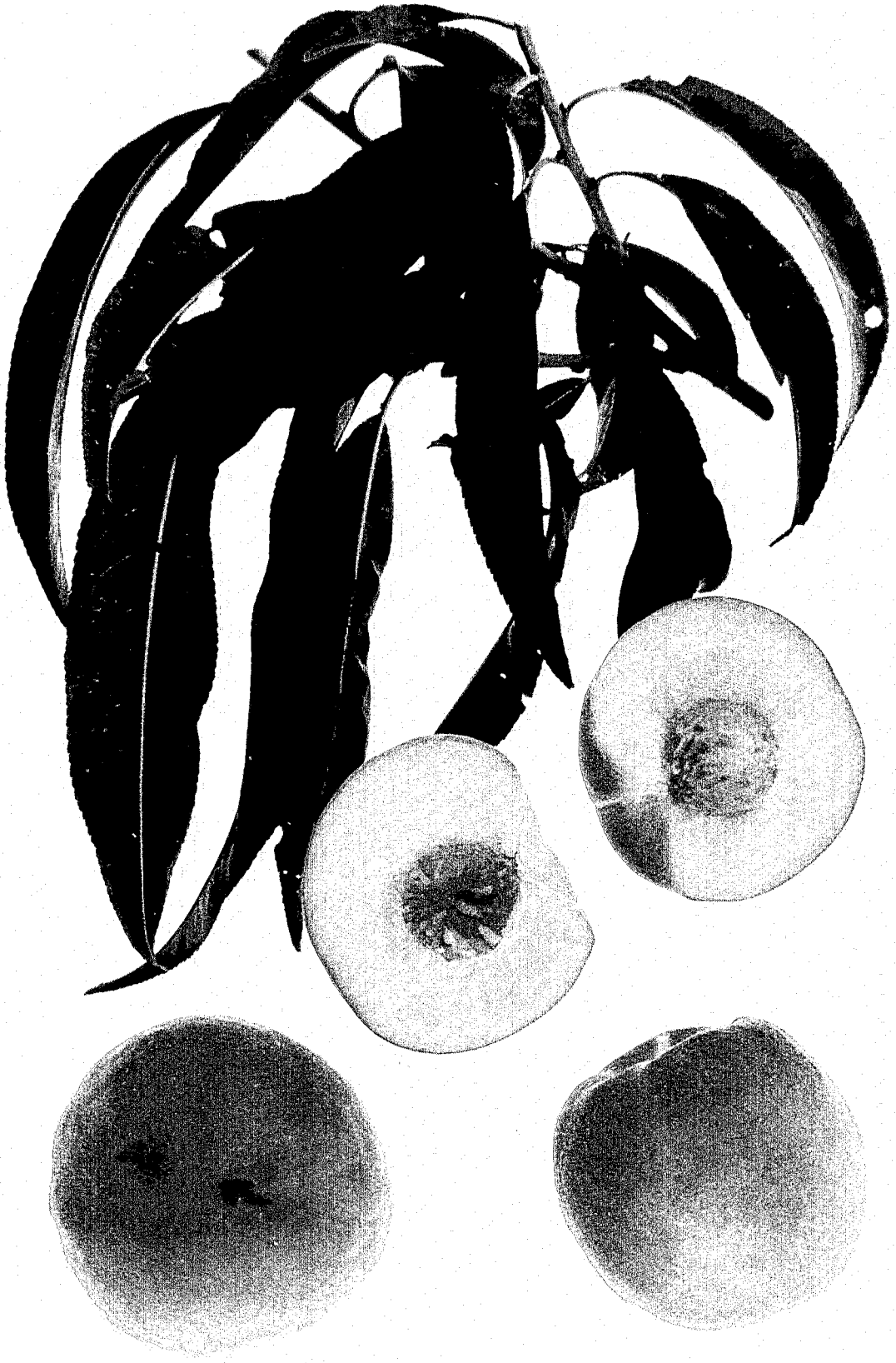

* * * * *